United States Patent [19]
Anderson

[11] Patent Number: 5,877,351
[45] Date of Patent: Mar. 2, 1999

[54] PREPARATION AND PURIFICATION PROCESS FOR 2-[(DIMETHYLAMINO) METHYL]-1-(3-METHOXPHENYL)-CYCLOHEXANOL AND ITS SALTS

[75] Inventor: Kenneth E. Anderson, Allegan, Mich.

[73] Assignee: Wyckoff Chemical Company, Inc., South Haven, Mich.

[21] Appl. No.: 997,915

[22] Filed: Dec. 24, 1997

[51] Int. Cl.$^6$ .................................................. C07C 209/84
[52] U.S. Cl. ............................................ 564/425; 564/438
[58] Field of Search ....................................... 564/438, 425

[56] References Cited

U.S. PATENT DOCUMENTS

| | | | |
|---|---|---|---|
| 3,652,589 | 3/1972 | Flick ................................ | 260/326.5 M |
| 3,830,934 | 8/1974 | Flick et al. ........................ | 424/330 |
| 5,414,129 | 5/1995 | Cherkez et al. ................... | 564/425 |
| 5,625,064 | 4/1997 | Andrews et al. .................. | 544/366 |
| 5,672,755 | 9/1997 | Lerman et al. .................... | 564/425 |

FOREIGN PATENT DOCUMENTS

| | | | |
|---|---|---|---|
| 997399 | 7/1965 | United Kingdom . | |

OTHER PUBLICATIONS

European Patent Application EP 0 778 262 A2, published Jun. 1997, Bulletin 1997/24, International Class C07C 213/10.

Primary Examiner—Brian M. Burn
Attorney, Agent, or Firm—Baker & Daniels

[57] ABSTRACT

A process for the isolation and purification of (RR,SS)-2-[(dimethylamino)methyl]-1-(3-methoxyphenyl) cyclohexanol and its salts from a Grignard reaction mixture which includes the (RR,SS) isomer, the (RS,SR) isomer and Grignard reaction side products. An aqueous solution of HBr is added to the reaction mixture to effect the selective precipitation of the (RR,SS) hydrobromide isomer from the mixture while the (RS,SR) isomer remains in solution. The precipitated (RR,SS)-2-[(dimethylamino)methyl]-1-(3-methoxyphenyl)cyclohexanol hydrobromide is converted to (RR,SS)-2-[(dimethylamino)methyl]-1-(3-methoxyphenyl) cyclohexanol hydrochloride.

13 Claims, No Drawings

PREPARATION AND PURIFICATION PROCESS FOR 2-[(DIMETHYLAMINO) METHYL]-1-(3-METHOXPHENYL)-CYCLOHEXANOL AND ITS SALTS

BACKGROUND OF THE INVENTION

The present invention relates to a process for the preparation and purification of (RR,SS)-2-[(dimethylamino) methyl]-1-(3-methoxyphenyl)cyclohexanol and its salts. More particularly, the present invention relates to an improved process for the purification and isolation of (RR, SS)-2-[(dimethylamino)methyl]-1-(3-methoxyphenyl) cyclohexanol and its salts from reaction mixtures containing the (RR,SS) isomer, the (RS,SR) isomer, and Grignard reaction side products.

The hydrochloride salt of (RR,SS)-2-[(dimethylamino) methyl]-1-(3-methoxyphenyl)cyclohexanol is commonly known as Tramadol. Tramadol is considered a non-addicting analgesic, and is indicated for the management of moderate to moderately severe pain.

The original preparation, isolation and purification of Tramadol was reported in Arzneimittel-Forsch./Drug Res. 28(I), Heft 1a, 107,114 (1978), and patented in British Patent 997,399 and U.S. Pat. No. 3,652,589. In this work, the compound is initially obtained from a Grignard reaction mixture as a mixture of the cis and the trans hydrochloride salts. The unwanted trans isomer is removed from the mixture by refluxing a slurry of this salt in wet dioxane, filtering while still hot, and repeating the procedure in anhydrous dioxane. A second filtration resulted in pure cis Tramadol hydrochloride. A disadvantage with this procedure results from the use of large quantities of dioxane. Dioxane has been listed as a carcinogen by the EPA, and has been linked to CNS depression and necrosis of the liver and kidneys.

Improved methods for separation of the cis and trans isomers have been described in two recent patent documents, both owned by Chemagis Ltd., of Bnei Brak, Israel. In the first of these, namely U.S. Pat. No. 5,414,129, the cis and trans isomers are separated from a Grignard reaction mixture by adding HCl (aqueous or anhydrous) to the crude reaction mixture in an organic solvent. This separation takes advantage of the selective precipitation of the cis (RR,SS) isomer from the reaction solution at a faster rate than the trans (RS,SR) isomer. According to the patent, a purity of 97.8% of the cis isomer is obtained after two recrystallizations. However, this indicates that over 2% of trans isomer remains. Furthermore, as stated in the later-published European Patent Application EP 0 778 262 (also owned by the assignee of the '129 patent), the process described in the '129 patent suffers from the disadvantage that the time interval between the end of separation of the (RR,SS) isomer and the start of the (RS,SR) isomer separation is variable, and seems to depend sharply on the composition of the crude mixture. Thus, according to the published European Patent Application, the yield and quality of the final product obtained from the purification process taught in the '129 patent may vary, and about 40% of the (RR,SS) isomer does not separate and remains in solution with the (RS,SR) isomer.

The process described in the European Patent Application EP 0 778 262 filed by Chemagis Ltd. uses a strong acid in an organic or aqueous medium to selectively dehydrate the (RS,SR) isomer, while the (RR,SS) isomer remains intact. The (RS,SR) isomer remains in the mother liquor upon crystallization of an amine salt of the (RR,SS) isomer. In this process, some of the trans (RS,SR) isomer is also converted to the cis (RR,SS) isomer. Yield losses have been found to be high with this process.

A reader should bear in mind that in the foregoing references of European origin, Tramadol is referred to as the trans isomer. However, when named according to IUPAC rules, Tramadol is the cis isomer. The present patent document follows IUPAC nomenclature rules, and thus, Tramadol is referred to herein as the cis isomer.

The known methods for preparation and/or purification of Tramadol suffer from significant disadvantages. For example, some methods use hazardous raw materials. Other methods require numerous steps, including multiple recrystallizations in order to obtain the desired product. Still other methods suffer from low yield, and low selectivity of the desired cis isomer.

Accordingly, it is desired to provide an improved process for the preparation and purification of (RR,SS)-2-[(dimethylamino)methyl]-1-(3-methoxyphenyl) cyclohexanol and its salts that uses generally safe ingredients, is highly selective for the desired cis isomer, and provides high yield of the desired end product.

SUMMARY OF THE INVENTION

The problems of the prior art are addressed by the present invention, wherein an improved process for the preparation and purification of (RR,SS)-2-[(dimethylamino)methyl]-1-(3-methoxyphenyl)cyclohexanol and its salts is provided. The inventive process may be performed in a single reactor vessel, provides high yield and high selectivity for the desired cis isomer, and utilizes generally safe ingredients.

The present invention, in one form thereof, provides a process for the isolation of (RR,SS)-2-[(dimethylamino) methyl]-1-(3-methoxyphenyl)cyclohexanol from a reaction mixture which includes the (RR,SS) isomer, the (RS,SR) isomer and Grignard reaction side products. A solution of hydrobromic acid is added to the reaction mixture in the presence of water or an organic solvent, thereby effecting the selective precipitation of (RR,SS)-2-[(dimethylamino) methyl]-1-(3-methoxyphenyl)cyclohexanol hydrobromide from the mixture. The hydrobromide salt is separated from the mixture, and thereafter converted to (RR,SS)-2-[(dimethylamino)methyl]-1-(3-methoxyphenyl) cyclohexanol hydrochloride.

The present invention, in another form thereof, comprises a process for preparing (RR,SS)-2-[(dimethylamino)methyl] -1-(3-methoxyphenyl)cyclohexanol hydrochloride. The process comprises preparing a reaction mixture comprising the (RR,SS) isomer, the (RS,SR) isomer, and Grignard reaction side products. The reaction mixture is mixed with a solution of hydrobromic acid in the presence of water or an organic solvent to selectively precipitate the (RR,SS) hydrobromide isomer, while the (RS,SR) isomer remains in solution. The (RR,SS) hydrobromide isomer is converted to the free base with NaOH, and is thereafter converted to the hydrochloride by reaction with hydrogen chloride.

The present invention, in yet another form thereof, comprises the compound (RR,SS)-2-[(dimethylamino)methyl]-1-(3-methoxyphenyl)cyclohexanol hydrobromide, which is an intermediate in the inventive process for preparation and purification of Tramadol.

The present invention, in still another form thereof, comprises a method for preparation of the compound (RR,SS)-2-[(dimethylamino)methyl]-1-(3-methoxyphenyl) cyclohexanol hydrobromide.

An advantage of the present invention is that it provides a process for the preparation and purification of (RR,SS)-

2-[(dimethylamino)methyl]-1-(3-methoxyphenyl) cyclohexanol and its salts that provides highly purified end products having in excess of 99.5% of the desired cis isomer.

Another advantage of the present invention is that it provides a process for preparation of Tramadol that may be performed under mild reaction conditions, and that provides a highly pure end product having in excess of 99.5% of the desired cis isomer of 2-[(dimethylamino)methyl]-1-(3-methoxyphenyl)cyclohexanol.

Still another advantage of the present invention is that it provides a process for preparation of Tramadol that provides high yields of the desired Tramadol end product.

Yet another advantage of the present invention is that it provides a process for the preparation and purification of Tramadol that avoids the use of toxic ingredients.

A still further advantage of the present invention is that it provides a process for preparation of the hydrobromide salt of 2-[(dimethylamino) methyl]-1-(3-methoxyphenyl)-cyclohexanol.

substantially all of the remaining impurities are removed, and the desired Tramadol hydrochloride salt is produced in essentially pure form, with no recrystallization required. Dependent upon the particular solvent used, purities approaching 100% of the desired cis isomer may be recovered.

An illustrative description of the inventive method follows:

Preparation of Crude Tramadol Base

The crude Tramadol base (III) comprising the (RR,SS) isomer, the (RS,SR) isomer and Grignard reaction side products is prepared via a Grignard reaction according to the following general formula:

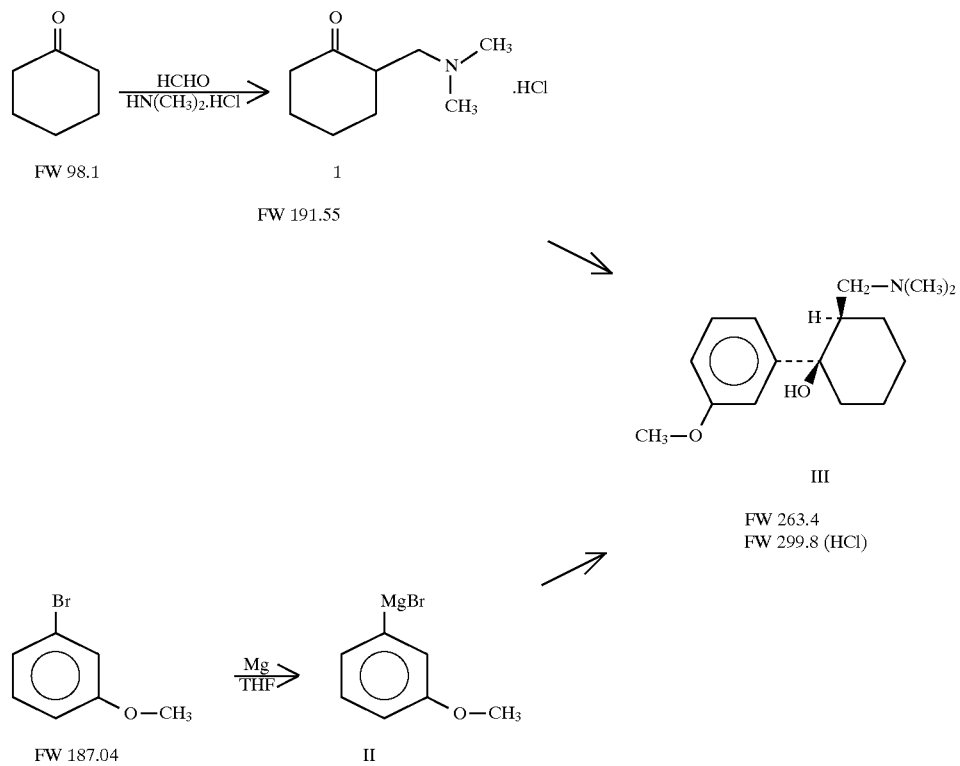

DETAILED DESCRIPTION OF THE INVENTION

The present invention provides an improved process for the preparation and purification of (RR,SS)-2-[(dimethylamino)methyl]-1-(3-methoxyphenyl) cyclohexanol and its salts. In the inventive method, highly purified Tramadol is isolated in the form of its hydrobromide salt from a reaction mixture comprising the (RR,SS) isomer, the (RS,SR) isomer and Grignard reaction side products by treating the crude reaction mixture with an aqueous solution of hydrobromic acid, in the presence of water or an organic solvent. Treatment of this mixture with HBr effects the selective precipitation of (RR,SS)-2-[(dimethylamino) methyl]-1-(3-methoxyphenyl)cylcohexanol hydrobromide from the mixture. The precipitated hydrobromide salt comprises in excess of 99.5% of the desired cis isomer. Upon converting the hydrobromide salt to the hydrochloride, The Mannich base (I) is prepared by reacting cyclohexanone with formaldehyde and dimethylamine hydrochloride to produce the hydrochloride salt of 2-dimethylamino methyl cyclohexanone. Methods of preparing this base are known in the art. For example, Mannich reported a method wherein excess cyclohexanone is reacted with one equivalent each of dimethylamine HCl and formaldehyde. (Ber. 53B, 1874–1880 (1920)). Grünenthal (Tramadol's innovator) reported a method wherein two equivalents of cyclohexanone were reacted with one equivalent each of dimethylamine HCl and formaldehyde, using glacial acetic acid as a solvent. This method used by Grünenthal was reported in the original work on Tramadol published in Arzneimittel-Forsch./Drug Res. Although either of these methods may be used in the inventive process to prepare the Mannich Base, the method of Grünenthal is preferred because it provides higher yields and is more manageable in the laboratory. For best results, the Mannich base hydrochloride is isolated from the Mannich reaction mixture by distillation, preferably vacuum distillation, followed by crystallization. Vacuum distillation was found to be an effective way to remove the impurities such as water, acetic acid and cyclohexanone from the system. Following distillation, acetone is added to the residue to produce a thick slurry. The slurry is cooled, collected and washed with acetone. The wetcake or dried material is then dissolved in water and converted to the free base by addition of 50% NaOH. The free base is extracted into toluene.

The Grignard reagent (II) may be prepared in conventional fashion. According to the stoichiometry reported in the literature, one equivalent of 3-bromoanisole is dissolved in THF (approximately 1.1 ml per gram), and this solution is slowly added to one equivalent of magnesium in THF (approximately 12.5 ml per gram). This reaction is strongly exothermic, and the 3-bromoanisole solution is added at a rate to maintain a reaction temperature of 55°–65° C. with cooling. When the addition is complete, the mixture is heated at reflux until all of the magnesium is consumed (about two hours), and then cooled to room temperature. The present inventor prefers to modify the conventional stoichiometry by adding about 1.03 equivalents of 3-bromoanisole neat to one equivalent of magnesium in THF (approximately 9.0–9.5 ml per gram). In this way, the use of the expensive THF component may be minimized. Although the Grignard reagent produced by this modified procedure is quite thick, it can be thinned by addition of toluene. The Tramadol resulting from reaction of this reagent with the Mannich base has an impurity profile and yield similar to that obtained when the more dilute Grignard reagent is used.

After the Grignard reagent is cooled, the Grignard reaction in commenced. The Mannich base (I) in toluene is added dropwise to the Grignard reagent (II), at a rate such that the temperature of the reaction mixture remains below about 20° C. with cooling. The reaction mixture is stirred at room temperature for about two hours, after which the mixture is quenched by adding dropwise a concentrated ammonium chloride solution using an ice bath to keep the temperature of the mixture below about 25° C. The layers are separated, and the toluene layer is distilled under vacuum to remove the THF and toluene solvents. At this point, the crude Tramadol base normally comprises a mixture of about 80–85% of the desired cis isomer, about 15–20% of the trans isomer, plus various impurities. The only significant impurity normally present in the reaction mixture (other than the trans isomer) is anisole, which is believed to be produced by reduction of the Grignard reagent by acidic protons on the ketone. For best results, the mixture should be purged with nitrogen upon completion of the vacuum distillation to remove most of the anisole.

Crystallization and Purification

The next step in the process is to purify the crude Tramadol base. In the method for isolating Tramadol from Grignard reaction side products described in the Chemagis Ltd. '129 patent referred to previously, the crude Tramadol base resulting from the Grignard reaction was directly converted to the hydrochloride by reacting the crude Tramadol base with a solution of hydrochloric acid, or with gaseous hydrogen chloride, in a medium molecular weight organic solvent. According to the patent, a mixture containing over 2% of the undesired trans isomer was obtained after two crystallizations. The purity results claimed in this patent could not be duplicated in the inventor's laboratory. Furthermore, the presence of at least 2% impurities renders this process unsuitable when used to obtain a drug product.

Modifications to this process were attempted using different solvents, and different amounts and rates of addition of HCl. No reliable, repeatable method for improving the selectivity of the cis isomer was found using this process.

Surprisingly, the present inventor found that by treating crude Tramadol base in a suitable solvent with hydrobromic acid, rather than with hydrochloric acid, the selectivity of the reaction for the desired cis isomer was significantly increased. In particular, (RR,SS)-2-[(dimethylamino)methyl]-1-(3-methoxyphenyl)cyclohexanol hydrobromide having a purity of at least 99.7% was crystallized out of the solution. This selectivity was repeatable with a wide variety of organic solvents. Furthermore, a purity of at least 99.5% could even be obtained in water solvent.

In general, the preferred solvents that may be utilized to selectively precipitate the desired cis isomer from the crude Tramadol base include water, as well as alcohols having between 1 and 6 carbon atoms, ketones having between 3 and 6 carbon atoms, and alkyl esters of organic acids having between 1 and 3 carbon atoms.

The highly-pure cis Tramadol hydrobromide salt is then isolated from the reaction mixture. Following isolation of the hydrobromide salt, this salt is converted to the hydrochloride for use as the drug product Tramadol. To convert the hydrobromide to the hydrochloride, the hydrobromide wetcake obtained from the crystallization is slurried in water and a suitable organic solvent such as toluene, and converted to the free base by adding a basic substance, such as 50% NaOH, to the slurry to raise the pH of the solution to at least 12. The layers are separated and the upper layer is distilled under vacuum to remove the toluene and residual water. The residue is dissolved in acetone having about 0.5% water. Anhydrous hydrogen chloride is added to a final pH range of 3.0–3.5 to effect the conversion to the hydrochloride salt.

The following examples are provided in order to more fully illustrate the process of the present invention:

EXAMPLE 1

192.0 grams of 3-bromoanisole were added to 24.3 grams of magnesium turnings in 220 ml of dry THF in a reaction vessel. About 5% of the 3-bromoanisole was added initially, and the mixture was stirred until the reaction started, as evidenced by a strong exotherm. The remainder of the 3-bromoanisole was then added at a rate as to maintain a temperature of about 55°–65° C. with cooling. After the addition was completed, the reaction mixture was heated at reflux until the magnesium was completely consumed. The reaction mixture was then cooled below 20° C. A mixture of 155.1 grams of 2-dimethylaminomethyl cyclohexanone and 150 ml of toluene was then added dropwise to the reaction mixture, maintaining the temperature of the reaction mixture below 20° C. The reaction mixture was stirred at room temperature for two hours, and a solution of 125 grams of ammonium chloride and 450 ml of water was added dropwise using an ice bath to keep the temperature below 25° C. The layers were separated, and the upper (toluene) layer was distilled under vacuum to remove the solvents. 200 ml of acetone was added to the residue, and the resulting solution cooled to room temperature. A solution of 48% Hydrobromic acid was added dropwise to the solution until a final pH range of 3.0–3.5 was obtained. The resulting slurry was cooled to below 10° C., filtered, and washed with cold acetone. Approximately 150 grams of pure (>99.8%), white cis 2-[(dimethylamino)methyl]-1-(3-methoxyphenyl)cyclohexanol hydrobromide wetcake was recovered.

The hydrobromide wetcake was then stirred with 300 ml of water, 100 ml of toluene, and sufficient 50% sodium hydroxide solution to raise the pH of the solution above 12.0. The layers were separated, and the lower layer was extracted with an additional 50 ml of toluene. The combined upper layers were distilled under vacuum to remove the solvent and residual water. 165 ml of acetone and 0.8 ml of water were added to the residue, and the resulting colorless solution was cooled to room temperature. Anhydrous hydrogen chloride was then added to a final pH range of 3.0–3.5. The resulting slurry was cooled to below 10° C., filtered, and washed with cold acetone to yield approximately 100 grams of pure Tramadol hydrochloride.

EXAMPLE 2

The Tramadol base was prepared as described in Example 1. In this example, water was used as the solvent for the Tramadol base. 25 ml of water was added to approximately 27 grams of Tramadol base containing roughly 11 % of the trans isomer. The mixture was stirred at 60° C., and one equivalent of 48% Hydrobromic acid was added dropwise to a final pH range of 3.0–3.5. The resulting slurry was cooled to below 10° C., filtered, and washed with water to yield approximately 24 grams of pure (>99.6%) off-white cis Tramadol hydrobromide. The hydrobromide wetcake may be converted to the hydrochloride as in Example 1.

EXAMPLE 3

The Tramadol base was prepared as in Example 1. In this example, isopropyl alcohol was used as the solvent. After distillation of the solvents, 100 ml of isopropyl alcohol (IPA) was added to the crude Tramadol base containing approximately 100 grams of mixed Tramadol isomers. The solution was cooled to room temperature, and 48% Hydrobromic acid was added dropwise to a final pH range of 3.0–3.5. The resulting slurry was cooled below 10° C., filtered and washed with cold IPA to yield approximately 73 grams of pure (>99.7%) white cis Tramadol hydrobromide.

EXAMPLE 4

In this example, the Tramadol hydrochloride base was prepared according to the procedure of Example 1, except that a 300 gallon batch size was used. After distillation of the solvents, 47 gallons of acetone was added to the crude Tramadol base mixture containing approximately 330 pounds of mixed Tramadol isomers. The solution was cooled to room temperature, and 48% Hydrobromic acid was added slowly to a final pH of below 3.5. The resulting slurry was cooled to below 10° C., collected by centrifugation, and washed with cold acetone to yield 201 pounds of pure (>99.7%), white cis Tramadol hydrobromide wetcake.

EXAMPLES 5–13

44 grams of crude Tramadol base which contained approximately 32 grams of the cis isomer and 8 grams of the trans isomer was dissolved in 44 ml of each of the solvents listed below. One equivalent of 48% hydrobromic acid was added dropwise, maintaining the temperature below 35° C. The batch was seeded with pure cis Tramadol hydrobromide after 1–5% of the addition was completed. (In the case of methanol, the seed dissolved until more than 70% of the addition was completed.) The resulting slurry was cooled to below 10° C., filtered and washed with cold acetone. The results are provided below:

| Example | Solvent | % cis Isomer | % trans Isomer | Yield (gm) |
| --- | --- | --- | --- | --- |
| 5 | Methanol | 99.9 | 0.1 | 17.0 |
| 6 | Ethanol | 99.9 | 0.1 | 18.1 |
| 7 | 1-Butanol | 99.9 | 0.1 | 21.5 |
| 8 | 1-Hexanol | 99.8 | 0.2 | 25.3 |
| 9 | 2-Butanone | 99.8 | 0.2 | 22.1 |
| 10 | 3-Pentanone | 99.8 | 0.2 | 26.9 |
| 11 | 2-Pentanone | 99.8 | 0.2 | 24.7 |
| 12 | Cyclohexanone | 99.8 | 0.2 | 19.2 |
| 13 | Ethyl Acetate | 99.7 | 0.3 | 26.4 |

While this invention has been described in its preferred embodiments, the present invention can be further modified within the spirit and scope of this disclosure. This description is therefore intended to cover any variations, uses, or adaptations of the invention using its general principles. Further, this description is intended to cover such departures from the present disclosure as come within known or customary practice in the art to which this invention pertains, and which fall within the limits of the appended claims.

What is claimed is:

1. A process for the isolation and purification of (RR,SS)-2-[(dimethylamino)methyl]-1-(3-methoxyphenyl)cyclohexanol hydrochloride from a reaction mixture including the (RR,SS) isomer, the (RS,SR) isomer and Grignard reaction side products, comprising reacting the mixture with an aqueous solution of hydrobromic acid in the presence of water or an organic solvent selected from the group consisting of alcohols having between 1 and 6 carbon atoms, ketones having between 3 and 6 carbon atoms, and alkyl esters of organic acids having between 1 and 3 carbon atoms to effect the selective precipitation of (RR,SS)-2-[(dimethylamino)methyl]-1-(3-methoxyphenyl)cyclohexanol hydrobromide from the mixture;

separating the precipitated (RR,SS)-2-[(dimethylamino)methyl]-1-(3-methoxyphenyl)cyclohexanol hydrobromide from the mixture;

converting the separated (RR,SS)-2-[(dimethylamino)methyl]-1-(3-methoxyphenyl)cyclohexanol hydrobromide to (RR,SS)-2-[(dimethylamino)methyl]-1-(3-methoxyphenyl)cyclohexanol hydrochloride; and separating the (RR,SS)-2-[(dimethylamino)methyl]-1-(3-methoxyphenyl)cyclohexanol hydrochloride.

2. The process of claim 1, wherein the organic solvent is selected from the group consisting of acetone, methanol, ethanol, isopropanol, 1-butanol, 1-hexanol, 2-butanone, 2-pentanone, 3-pentanone, cyclohexanone and ethyl acetate.

3. The process of claim 1, wherein the solvent is water.

4. The process of claim 1, wherein the separated (RR,SS)-2-[(dimethylamino)methyl]-1-(3-methoxyphenyl)cyclohexanol hydrobromide is converted to (RR,SS)-2-[(dimethylamino)methyl]-1-(3-methoxyphenyl)cyclohexanol hydrochloride by mixing the (RR,SS) hydrobromide isomer in water and an organic solvent, adding a basic solution to liberate the free (RR,SS)-2-[(dimethylamino)methyl]-1-(3-methoxyphenyl)cyclohexanol base in the solvent layer, separating and drying the solvent layer, dissolving the residue from the dried layer in a solvent, and adding hydrogen chloride to the solvent and dissolved residue to reduce the pH to about 3.0–3.5 and thereby crystallize the (RR,SS)-2-[(dimethylamino)methyl]-1-(3-methoxyphenyl)cyclohexanol hydrochloride isomer.

5. The process of claim 4, wherein the basic solution comprises about 50% NaOH and wherein the hydrogen chloride added comprises anhydrous hydrogen chloride.

6. The process of claim 5, wherein the separated layer including the free base is dried by vacuum distillation.

7. The process of claim 4, wherein the residue from the dried layer is dissolved in acetone having about 0.5% water.

8. The process of claim 1, wherein the Grignard reaction mixture comprises a product of a mixture between a Mannich base and a Grignard reagent, said Mannich base being prepared by reacting about two equivalents of cyclohexanone with about one equivalent each of dimethylamine hydrochloride and formaldehyde in acetic acid solvent, vacuum distilling excess cyclohexanone and acetic acid, and dissolving the distilled residue in an organic solvent.

9. The process of claim 8, wherein the Grignard reaction mixture is purged with nitrogen prior to the reaction with hydrobromic acid.

10. A process for preparing (RR,SS)-2-[(dimethylamino) methyl]-1-(3-methoxyphenyl)cyclohexanol hydrochloride, comprising:

preparing a reaction mixture comprising the (RR,SS)-2-[(dimethylamino)methyl]-1-(3-methoxyphenyl) cyclohexanol isomer, the (RS,SR) isomer, and Grignard reaction side products;

reacting the reaction mixture with a solution of hydrobromic acid in the presence of water or an organic solvent selected from the group consisting of alcohols having between 1 and 6 carbon atoms, ketones having between 3 and 6 carbon atoms, and alkyl esters of organic acids having between 1 and 3 carbon atoms to effect the selective precipitation of (RR,SS)-2-[(dimethylamino)methyl]-1-(3-methoxyphenyl) cyclohexanol hydrobromide from the mixture;

separating the (RR,SS)-2-[(dimethylamino)methyl]-1-(3-methoxyphenyl)cyclohexanol hydrobromide from the mixture; and converting the separated (RR,SS)-2-[(dimethylamino) methyl]-1-(3-methoxyphenyl)cyclohexanol hydrobromide to (RR,SS)-2-[(dimethylamino)methyl]-1-(3-methoxyphenyl)cyclohexanol hydrochloride.

11. The process of claim 10, wherein the reaction mixture comprises a Mannich base and a Grignard reagent, said Mannich base being prepared by reacting about two equivalents of cyclohexanone with about one equivalent each of dimethylamine hydrochloride and formaldehyde in acetic acid solvent, vacuum distilling excess cyclohexanone and acetic acid, and adding acetone to the residue.

12. A process for preparing (RR,SS)-2-[(dimethylamino) methyl]-1-(3-methoxyphenyl)cyclohexanol hydrobromide, comprising:

reacting 2-dimethylaminomethyl cyclohexanone with a Grignard reagent to obtain a reaction mixture comprising the (RR,SS)-2-[(dimethylamino)methyl]-1-(3-methoxyphenyl)cyclohexanol isomer, the (RS,SR) isomer, and Grignard reaction side products;

reacting the reaction mixture with a solution of hydrobromic acid in the presence of water or an organic solvent selected from the group consisting of alcohols having between 1 and 6 carbon atoms, ketones having between 3 and 6 carbon atoms, and alkyl esters of organic acids having between 1 and 3 carbon atoms to effect the selective precipitation of (RR,SS)-2-[(dimethylamino)methyl]-1-(3-methoxyphenyl) cyclohexanol hydrobromide from the mixture; and separating the (RR,SS)-2-[(dimethylamino)methyl]-1-(3-methoxyphenyl)cyclohexanol hydrobromide from the mixture.

13. The process of claim 12, wherein the organic solvent is selected from the group consisting of acetone, methanol, ethanol, isopropanol, 1-butanol, 1-hexanol, 2-butanone, 2-pentanone, 3-pentanone, cyclohexanone and ethyl acetate.

* * * * *

UNITED STATES PATENT AND TRADEMARK OFFICE
CERTIFICATE OF CORRECTION

PATENT NO. : 5,877,351
DATED : March 2, 1999
INVENTOR(S) : Kenneth E. Anderson

It is certified that error appears in the above-indentified patent and that said Letters Patent is hereby corrected as shown below:

On the title page and column 1, line 3,
   In Item [54], line 3 of the title, delete "methoxphenyl", and replace with --methoxyphenyl--.

Signed and Sealed this

Twenty-eighth Day of September, 1999

Attest:

Q. TODD DICKINSON

*Attesting Officer*    *Acting Commissioner of Patents and Trademarks*